United States Patent [19]
Ragsdale

[11] Patent Number: 5,729,426
[45] Date of Patent: Mar. 17, 1998

[54] TRANSFECTION HIGH-VOLTAGE CONTROLLER

[75] Inventor: Charles W. Ragsdale, Concord, Calif.

[73] Assignee: Bio-Rad Laboratories, Hercules, Calif.

[21] Appl. No.: 630,308

[22] Filed: Apr. 10, 1996

Related U.S. Application Data

[62] Division of Ser. No. 260,654, Jun. 16, 1994, Pat. No. 5,564,035.

[51] Int. Cl.$^6$ .................................................... H01G 4/38
[52] U.S. Cl. ................................................... 361/328
[58] Field of Search ........................... 323/282; 327/536; 361/280, 281, 328, 330

[56] References Cited

U.S. PATENT DOCUMENTS

| | | | |
|---|---|---|---|
| 4,999,565 | 3/1991 | Nilsson | 323/210 |
| 5,077,486 | 12/1991 | Marson et al. | 307/95 |

*Primary Examiner*—Matthew V. Nguyen
*Attorney, Agent, or Firm*—Townsend and Townsend and Crew LLP

[57] ABSTRACT

The present invention provides apparatus and method for simply and efficiently improving prior art transfection systems. The present invention is a transfection high-voltage controller that provides features for measuring actual load resistance, and compensating for any effects of a limit impedance in series with the load. Additionally, the transfection controller of the present invention measures actual effective capacitance of a storage capacitor, or capacitors, and through use of an expansion module, effectively provides the user with a set of user-selectable capacitors having an effective ±10% tolerance when the tolerance of the individual electrolytic capacitors is ±20%. The preferred embodiment incorporates two sections. One section of the system handles 200–2500V and another section handles low voltages (50–500V). The transfection controller includes an improved hi-joule switch that operates in a low-voltage, high-current mode with a low dropout voltage (for use with the 500V (maximum) electrolytic capacitors. Further, additional protective circuitry in the form of a crowbar circuit, will not only prevent charging of the storage capacitor unless a safety switch is operated, charge from the capacitor is shunted to ground should the charging operation be interrupted, or if power is removed from the transfection system.

3 Claims, 7 Drawing Sheets

TRANSFECTION HIGH-VOLTAGE CONTROLLER

This is a Division of application Ser. No. 08/260,654 filed Jun. 16, 1994, now U.S. Pat. No. 5,564,035.

CROSS-REFERENCE TO RELATED APPLICATIONS

The subject matter of this application is related to U.S. Pat. No. 4,750,100, and is hereby expressly incorporated by reference for all purposes.

BACKGROUND OF THE INVENTION

The present invention relates generally to transfection and cell fusion, and, more particularly, to an apparatus and method for directing high-voltage currents to a suspension of cells and DNA, usually contained in a cuvette.

In the biotechnology field, it is known to introduce cloned DNA into mammalian and other cells using a high-voltage electrical discharge. This procedure, commonly referred to as "transfection," typically involves creation of a suspension of cells in a phosphate-buffered saline (PBS) solution and addition of cloned DNA. A high-voltage pulse applied to the suspension from a pulse generator causes the cells to take up and express the exogenous DNA. Various pulse generators are available for this purpose.

Figure 1:
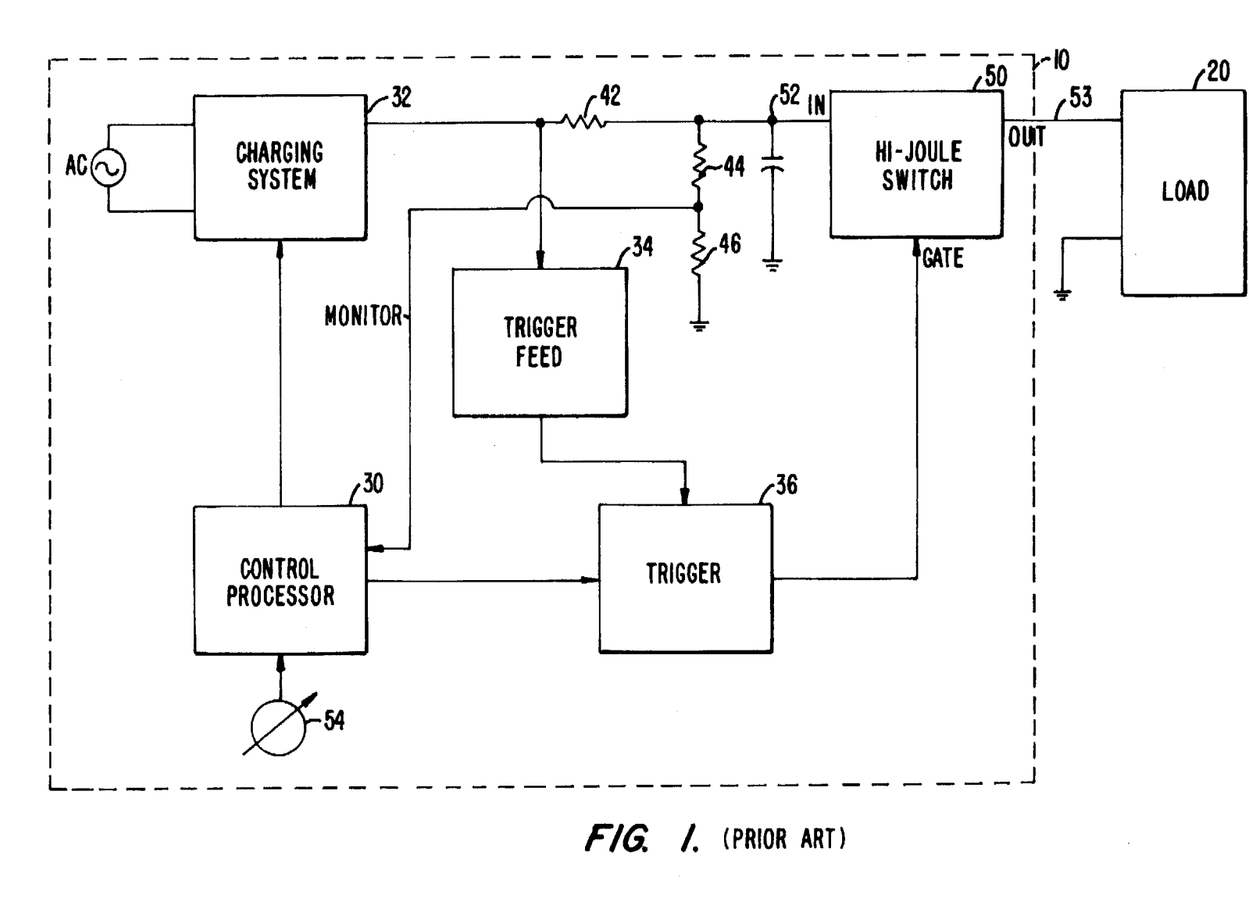
FIG. 1 is a schematic diagram of a conventional high-voltage transfection system.

The incorporated US patent referenced above provides a transfection high-voltage controller capable of directing a high-voltage current to a suspension of cells and DNA. FIG. 1 is a block schematic diagram of one preferred embodiment for a transfection system 10 disclosed therein for supplying voltage and current to a load 20. Transfection system 10 includes a control processor 30, a charging system 32, a trigger feed 34, a trigger 36, a capacitor 40, a first resistor 42, a second resistor 44, a third resistor 46 and a hi-joule switch 50.

Control processor 30 asserts a control signal to charging system 32 to initiate generation of a charging current. Trigger feed 34 operates on a voltage level present at an output port of the charging system. Trigger feed 34 includes a charge storage device to provide trigger 36 with an appropriate trigger energy.

Resistor 42 is connected to the output port of charging system 32 and to a charging node 52. Resistor 44 is connected between node 52 and ground. Resistor 42 limits current flow into node 52 to permit use of a smaller transformer in charging system 32. Capacitor 40 is coupled between node 52 and ground, and hi-joule switch 50 has an input terminal coupled to node 52. Resistor 44 in series with resistor 46 gradually discharges charge stored on capacitor 40. A monitor signal for control processor 30 is generated by resistor 44 and resistor 46.

Hi-joule switch 50 typically includes a semiconductor-controlled rectifier (SCR) (or silicon-controlled rectifier), as is well known. Hi-joule switch 50 provides an output voltage and current at its output terminal in response to an input gate signal. Once triggered, the charge/energy stored in capacitor 40 is directed through hi-joule switch 50 and into load 20 via a load line 53. Load 20 is commonly a grounded cuvette designed to contain cell suspensions, and the like.

Control processor 30 is connected to trigger 36 and will assert a trigger signal to trigger 36. Responsive to the trigger signal, trigger 36 directs the stored trigger energy as the gating signal for hi-joule switch 50. Typically, the gating signal needs to be a higher voltage than the voltage levels conveniently produced by control processor 30.

Transfection system 10 also includes a manual control unit 54 for setting desired voltage levels and for initiating operation. Typically, manual control unit 54 includes two independent, normally open switches, that both must be held closed in order to operate the system. Such a system reduces the risk of electrical shock to the operator.

In operation, control processor 30 asserts the control signal to the charging system when a user activates manual control 54. Charging system 32 charges capacitor 40 to a voltage level above the prescribed voltage level set by control unit 54, without triggering hi-joule switch 50 as determined by the monitor voltage. Control processor 30 deasserts the control signal to charging system 32 and waits for the voltage level at node 53 (as determined from the monitor voltage) to fall to the proper level, discharged through resistor 44 and resistor 46. When the voltage is correct, control processor 30 asserts the trigger signal to trigger 36, which in turn asserts the gating signal for hi-joule switch 50.

Responsive to the gating signal, hi-joule switch 50 directs the charge stored on capacitor 40 to load 20 via load line 53. The output voltage from hi-joule switch 50 is exponentially decaying, as is well known, and is a function of the capacitance of capacitor 40 and the resistance of load 20.

Transfection system 10 is capable of supplying voltages in excess of 3,000 volts and currents in excess of 1,000 amps. Due to the magnitude of the voltages and currents involved, and the requirement that the equipment be frequently manipulated by human operators, it is a continuous objective to improve the associated safety features and procedures.

As described above, transfection system 10 uses a semiconductor-controlled rectifier (SCR) (or silicon-controlled rectifier) hi-joule switch. This type of apparatus remains the only practical device for delivering clean waveforms at over 1000 ampere currents. Adding several SCR cells in series produces a high-voltage switch. The nature of an SCR is to deliver current up to its fusing current. Above this point, the SCR continues to deliver current, but as a dead-short. Once triggered, the SCR will not turn off until an input current drops below its holding current.

Because of the magnitude of the voltages and currents involved, it is desirable to control output current from the SCR after obtaining the desired output current. As described above, it is futile to try to limit output current by turning the SCR off when output current from the SCR reaches a desired level. Also, due to the potential range of currents involved, it is impractical to use current diverters.

While the load resistance will vary, dependent upon many factors, there are times that the effective resistance of the load will be a minimum of about twenty ohms. The maximum voltage is typically about 2500 volts and therefore the maximum current is normally about 125 amperes. Unfortunately, because of the magnitude of the voltages, an arc-over will sometimes occur, reducing the load (cuvette) resistance to effectively zero ohms. The discharge of the transfection current without resistance can damage the equipment, fuse the SCRs and increase risks to personnel operating the equipment.

It is known to include a limit impedance in series with the load in order to limit maximum current and to thereby decrease risks associated with arc-overs. Such a limit impedance would be added between hi-joule switch 50 and load 20 in load line 53. Even though the series impedance is on the order of about 1.5 ohms, when the cuvette resistance is low, the limit impedance can create a significant voltage drop, altering the actual voltage level applied to the load from the desired level stored on capacitor 40.

The transfection apparatus shown in FIG. 1 includes manual switch 54 for manually operating transfection system 10. In conventional systems during manual operations, it is known to require use of two pulse switches as described above. In order to charge capacitor 40, both switches must be pressed and held together. Such a system works to reduce the chance an operator will contact high voltage portions of the equipment during operation, as long as the charge and discharge processes occur without interruption. If an operator stops the operation short of capacitor discharge, then dangerous voltage levels may be present in capacitor 40.

In order to produce accurate results with transfection system 10, a precise charge/energy must be applied to load 20. In order to accurately determine the precise charge/energy stored in capacitor 40, an accurate capacitance value is necessary. Unfortunately, because of the magnitude of the charge/energy that capacitor 40 must store, the only feasible option up to the present for producing long time constants (up to 3.5 seconds) has been to use electrolytic capacitors. It is prohibitively expensive to obtain precision film capacitors of the size required for long time constants in a transfection system. However, the use of long time constants requires maximum voltages of only 500V which is possible for electrolytics. For high-voltage (2500V) experiments, the time constant required is shorter (50 MSEC or less) so that precision (±5% or ±10%) film capacitors are feasible. As a consequence, conventional long time constant transfection systems use capacitors with a standard ±25% tolerance. The state of the art for electrolytic capacitors is about ±20%. Such variations and imprecision in capacitance of storage capacitor 40 reduce the effectiveness of conventional transfection systems since different cells may require specific time-energy delivery.

The lack of precision of electrolytic capacitors is also a problem when providing capacitor expansion modules for transfection system 10. When using transfection system 10, fine control of different levels of charge/energy are required for different applications. It is desirable to provide a set of capacitors that are user selectable in order to obtain desired transfection energy profiles.

In some applications, the desired output voltage will be relatively small. While the SCR is particularly effective as a switch for high voltage and current levels, the SCR can be problematic when using low voltages. For example, sometimes the actual load can be about 1000 ohms. A typical holding current for an SCR is about 60 milliamperes. That requires that the voltage at node 53 be greater than about 60 volts. When the voltage at node 53 falls below 60 volts, with a 1000 ohm load, some conventional hi-joule switches will drop out and truncate the output waveform. In practice, it is desirable that operating voltages for an SCR used in the present application exceed 200 volts for best fidelity. Therefore, it is desirable to provide a hi-joule switch that is capable of operating at both high and low voltage levels.

SUMMARY OF THE INVENTION

The present invention provides apparatus and method for simply and efficiently improving prior art transfection systems. The present invention is a transfection high-voltage controller that provides features for measuring actual load resistance, and compensating for any effects of a limit impedance in series with the load. Additionally, the transfection controller of the present invention measures actual effective capacitance of a storage capacitor, or capacitors, and through use of an expansion module, effectively provides the user with a set of user-selectable capacitors having an effective ±10% tolerance when the tolerance of the individual electrolytic capacitors is ±20%.

The preferred embodiment incorporates two sections. One section of the system handles 200–2500V and another section handles low voltages (50–500V). The transfection controller includes an improved hi-joule switch that operates in a low-voltage, high-current mode with a low dropout voltage (for use with the 500V (maximum) electrolytic capacitors. Further, additional protective circuitry in the form of a crowbar circuit, will not only prevent charging of the storage capacitor unless a safety switch is operated, charge from the capacitor is shunted to ground should the charging operation be interrupted, or if power is removed from the transfection system.

According to one aspect of the invention, the preferred embodiment of a transfection control system for directing a high-voltage current profile to a chemical solution includes a hi-joule switch having a gate, an input and an output. A charge storing device coupled to the input provides the high-voltage current. A limit impedance between the output of the hi-joule switch and the load (chemical solution) provides arcover protection. A resistance measuring circuit is coupled to a node between the limit impedance and the chemical solution to measure resistance of the load prior to activation of the hi-joule switch. A control processor controls the voltage level at the charge storing device, and when the voltage level at the charge storing device is high enough to compensate for the drop across the limit impedance, the control processor triggers the hi-joule switch. Triggering the hi-joule switch directs the stored charge into the chemical solution at the desired high-voltage level.

According to other aspects of the invention, a crowbar switch is coupled to the charge storing device to dissipate the stored charge rapidly to ground. The crowbar is activated when a pulse switch, during manual control, is released, or when power is removed from the transfection system. The crowbar circuit permits accurate measurement of the actual capacitance, or the time constant, of the charge storing device during a procedure closely simulating actual use. This aspect of the invention includes use of a window comparator to activate an oscillator during a specific time window of charge dissipation. The time window is about equal to a period for the voltage on the charge storing device to fall to a 1/e reference value. A counter accumulates a total number of transitions from a periodic signal generated by the oscillator. The total number of transitions is proportional to the window and thus the time constant.

By dissipating the stored charge through the crowbar circuit (and using a predetermined resistor), monitoring the voltage on the charge storage device provides a total number of transitions that is proportional to the capacitance of the charge storing device.

According to still another aspect of the invention, a hi-joule switch includes a semiconductor-controlled rectifier (SCR) (silicon controlled rectifier) in parallel with a bipolar transistor. The SCR provides drive capacity for high-voltage currents that exceed the relatively low drive capability of the bipolar transistor. Similarly, the bipolar transistor provides low drive capability when the high-voltage current levels are less than a holding current of the SCR.

According to yet another aspect of the invention, it includes a capacitor expansion module for use in a transfection system. The expansion module includes a plurality of capacitor cells that are electronically selectable. Each cell of the expansion module includes a capacitor, a power diode, and a power FET. The diode is coupled to the capacitor to permit discharge current only. Activation of the FET permits charging current, with capacitors being charged only in those cells having an activated FET.

Reference to the remaining portions of the specification, including the drawing and claims, will realize other features and advantages of the present invention. Further features and advantages of the present invention, as well as the structure and operation of various embodiments of the present invention, are described in detail below with respect to accompanying drawing. In the drawing, like reference numbers indicate identical or functionally similar elements.

DESCRIPTION OF THE PREFERRED EMBODIMENT

Figure 2:
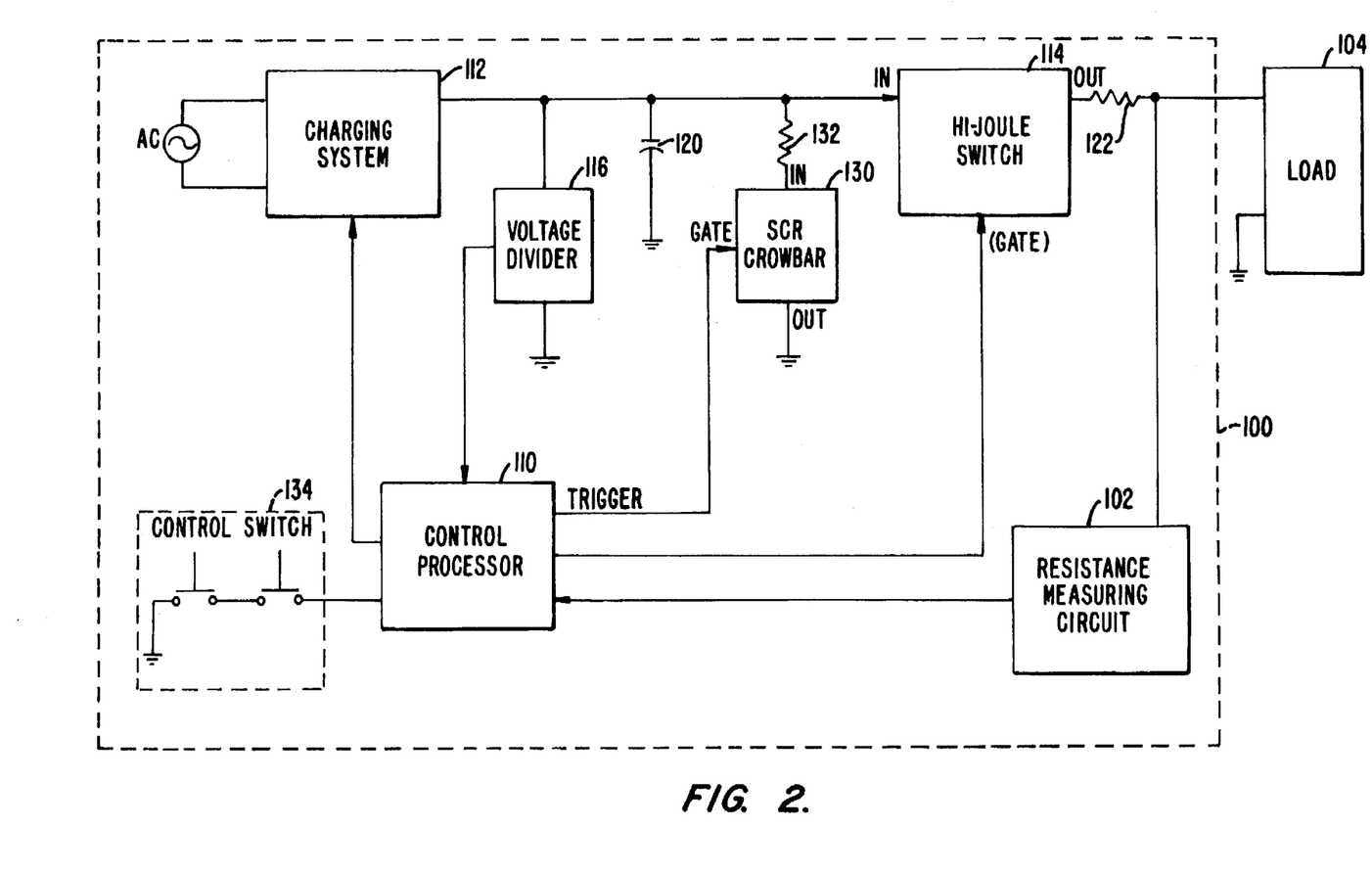
FIG. 2 is a schematic diagram of a preferred embodiment of the present invention for a high-voltage transfection system including a load resistance measuring apparatus.

FIG. 2 is a schematic diagram of a preferred embodiment of the present invention for a high-voltage transfection system 100 including a load-resistance measuring apparatus 102 for measuring a resistance of a load 104. Transfection system 100 includes a control processor 110, a charging system 112, a hi-joule switch 114, a voltage divider 116, a storage capacitor 120, a limit resistor 122, a shunt circuit including an SCR crowbar 130 with a series resistor 132, and an operating control switch 134. Control processor 110 includes a microprocessor for implementing the features herein described. SCR crowbar 130 includes an SCR.

Control processor 110 provides a charging signal to charging system 112. Charging system 112 is a high-voltage switching power converter circuit that delivers essentially constant current at an output port. Storage capacitor 120 is coupled between the output port of charging system 112 and ground. Voltage divider 116 is coupled between the output port of charging system 112 and ground, with a tap terminal coupled to control processor 110.

Hi-joule switch 114 includes a input port (anode), an output port (cathode) and a gate port. The input port is coupled to the ungrounded terminal of storage capacitor 120, the gate port is coupled to control processor 110, and the output port is coupled to limit resistor 122. SCR crowbar 130 includes an input port (anode), an output port (cathode) and a gate port. Series resistor 132 is coupled to the input port of hi-joule switch 114 and to the input port of crowbar circuit 130. The output port of SCR crowbar 130 is coupled to ground, and the gate port is coupled to control processor 110.

Limit resistor 122 is series-coupled between the output port of hi-joule switch 114 and load 104. Limit resistor 122 typically has a very low resistance, on the order of about 1.5 ohms. In the preferred embodiment in which there is a high-voltage section (200–2500V) and a low-voltage section (50–500V), 0.5 ohms is used for the resistance of the limit resister 122 when operating the low-voltage section and 1.5 ohms when operating the high-voltage section. Load resistance measuring apparatus 102 is coupled to a node between limit resistor 122 and load 104. Load resistance measuring apparatus 102 includes an oscillator for generating a low-amplitude 20 KHz signal. Load resistance measuring circuit 102 operates in well-known fashion to inject the low amplitude signal into load 104 to establish the resistance of the load. However, the measuring system is protected against high-voltage produced during pulse delivery. Measured resistance results are provided to control processor 110.

Figure 3:
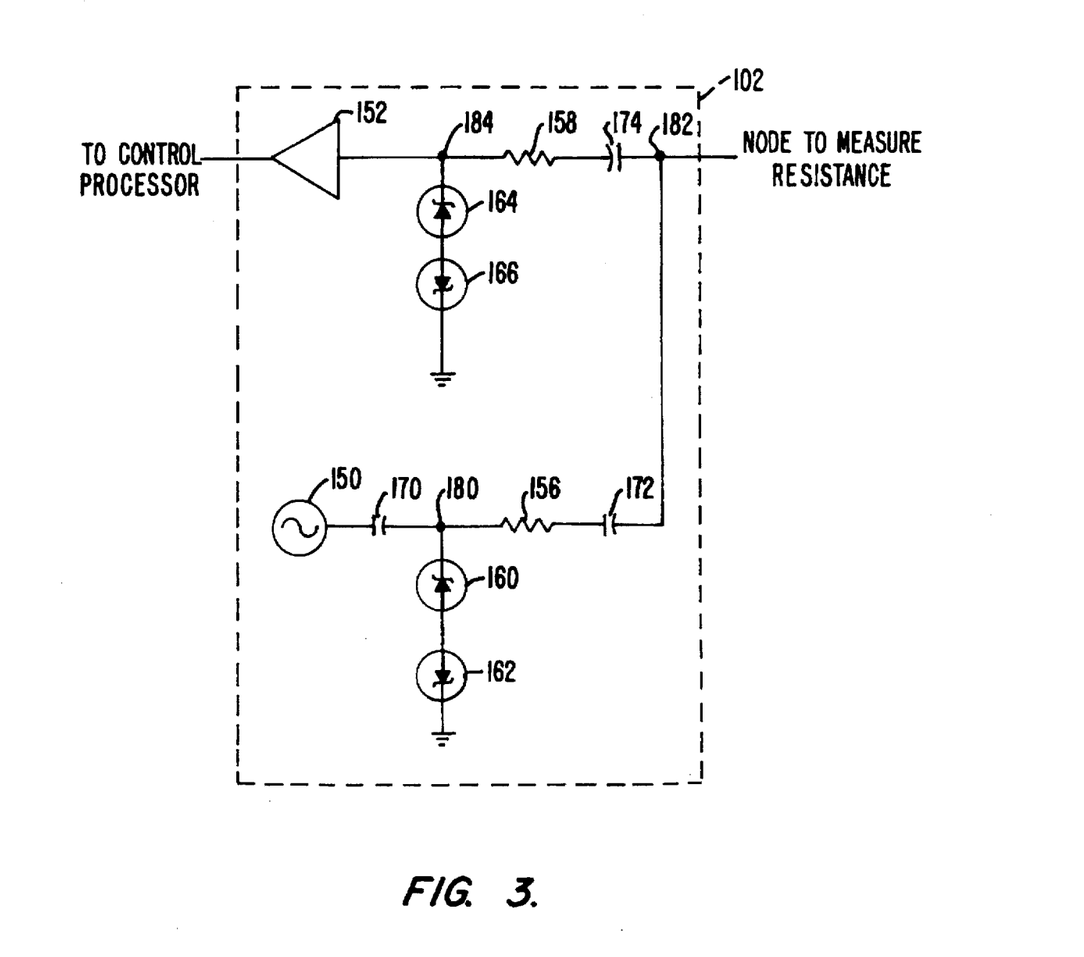
FIG. 3 is a detailed schematic of a preferred embodiment of the resistance measuring circuit shown in FIG. 2.

FIG. 3 is a detailed schematic diagram of a preferred embodiment for the resistance measuring circuit 102 shown in FIG. 2. Resistance measuring circuit 102 includes an oscillator 150, a bandpass amplifier 152, two high-voltage resistors (resistor 156 and resistor 158), four zener diodes (diode 160, diode 162, diode 164, and diode 166), and three capacitors (capacitor 170, capacitor 172, and capacitor 174). An output of oscillator 150 is coupled through capacitor 170 to a node 180. A cathode of diode 160 is coupled to node 180 and an anode of diode 160 is coupled to an anode of diode 162, having a cathode coupled to ground.

Resistor 156 and capacitor 172 are coupled in series between node 180 and a node 182, with resistor 156 connected to node 180 and capacitor 172 connected to node 182. The resistance to be measured, such as for example, the resistance of load 104 shown in FIG. 2, is coupled to node 182.

Capacitor 174 and resistor 158 are series coupled between node 182 and a node 184, with capacitor 174 connected to node 182 and resistor 158 connected to node 184. Diode 164 and diode 166 each include an anode and a cathode. The anodes are connected to each other, with the cathode of diode 164 connected to node 184 and the cathode of diode 166 connected to ground.

Bandpass amplifier 152 includes an input, an output and a range select input (not shown). The input of amplifier 152 is connected to node 184. The output of amplifier 152 is connected to an analog-to-digital (A/D) converter (not shown) of control processor 110. Bandpass amplifier provides a gain of about 100–400.

In operation, resistance measuring circuit 102 injects sine waves from oscillator 150, having a frequency of about 20 KHz and an amplitude of about fifty millivolts, into node 182. Bandpass amplifier 152 (an AC amplifier) recovers a voltage from node 182 that is roughly proportional to the resistance of load 104. The analog output voltage is provided to control processor 110. Control processor 110 digitizes the output value from amplifier 152. By use of a look-up table (not shown), control processor 110 linearizes the resistance values to determine the resistance of load 104. The range select switch permits resistance measuring circuit 102 to measure resistance in the range of 5–1,000 ohms.

Operating control switch 134 includes two series-connected pulse switches interposed between an input of control processor 110 and ground. To operate transfection system 100, a user must press and hold each of the pulse switches of control switch 134.

In operation, operating control switch 134 causes control processor 110 to assert a control signal to charging system 112 to have charging system 112 produce and deliver its output current. The output current of charging system 112 charges storage capacitor 120, increasing the voltage at the input of hi-joule switch 114. Control processor 110 monitors the voltage level at the input of hi-joule switch 114 via feedback from voltage divider 116. When the desired voltage level has been reached, control processor deasserts the control signal to charging system 112 and triggers hi-joule switch 114. Control processor 110 triggers hi-joule switch 114 by asserting the trigger signal to the gate port. Triggering hi-joule switch 114 couples the charge/energy stored in storage capacitor 120 to load 104 through limit resistor 122.

Thereafter, storage capacitor 120 discharges through load 104 until most of its stored charge is depleted. The amount of depletion during discharge through load 104 depends upon the holding current of hi-joule switch 114. Limit resistor 122 limits the maximum current load.

To ensure that limit resistor 122 does not adversely affect the magnitude of the applied voltage to load 104, load resistance measuring apparatus 102 determines the actual load resistance. Resistance measuring circuit 102 provides control processor 110 with the resistance measurement of the load.

Since control processor 110 thereafter knows the actual load resistance, and the value of limit resistor 122, control processor 110 permits the voltage level on storage capacitor 120 to rise to a higher level to compensate for the voltage drop across limit resistor 122. Providing for quantitatively-determined boosted voltage levels on storage capacitor 120 permits transfection system 100 to produce accurate output voltages even when using limit resistor 122. The limit resistor 122 enables transfection system 100 to tolerate arc-over without damage.

Shown in FIG. 2 is the crowbar shunt circuit coupled to the input port of hi-joule switch 114. The purpose of SCR crowbar 130 is to dump charge stored in storage capacitor 120 by directing the stored charge to ground. In operation, asserting the trigger signal to SCR crowbar 130 causes SCR crowbar to function as a low-resistance switch. SCR crowbar 130 remains on as long as the input current exceeds the holding current. When the current decreases, SCR crowbar automatically turns itself off. Normal current levels resulting from discharge of capacitor 120 are typically much higher than the holding current. Thus, SCR crowbar 130 effectively removes potentially dangerous charge levels stored on storage capacitor 120.

The use of series resistor 132 limits the magnitude of the input current into SCR crowbar 130. By limiting the input current into SCR crowbar 130, SCR crowbar 130 can use smaller, less-expensive SCR devices in its construction. In the preferred embodiment, series resistor 132 has a resistance of about 1000 ohms.

As described above, transfection system 100 will only operate when control switch 134 is properly activated. Control processor 110 will detect whether one of the pulse switches of control switch 134 is released before capacitor 120 is discharged through hi-joule switch 114 into load 104. Releasing one or both of the pulse switches results in control processor 110 triggering SCR crowbar 130 to remove any charge stored on capacitor 120.

Figure 4:
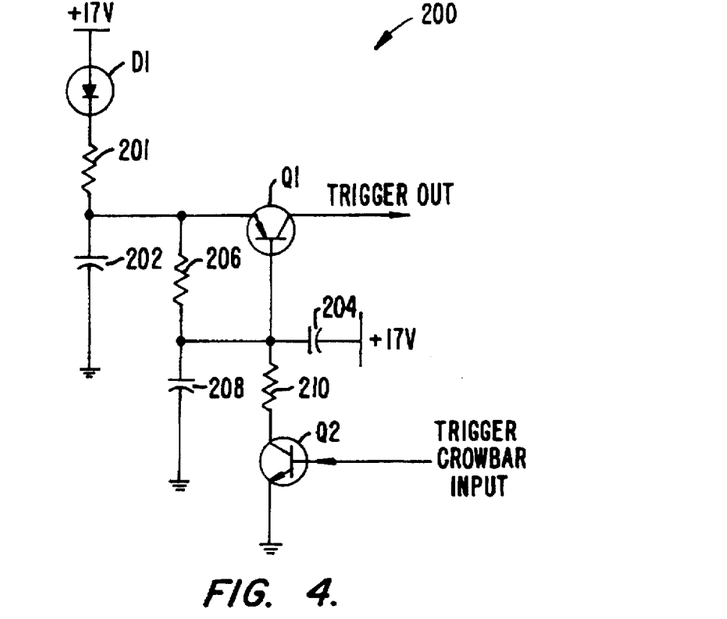
FIG. 4 is a detailed schematic diagram of a crowbar trigger circuit according to a preferred embodiment.

Not only is it desirable to trigger SCR crowbar 130 should a pulse switch be released, the preferred embodiment of the present invention triggers SCR crowbar 130 should power be turned off. FIG. 4 is a detailed schematic diagram of a crowbar trigger circuit 200 according to a preferred embodiment. Trigger circuit 200, in the preferred embodiment, is incorporated into control processor 110 and operates to assert trigger out should operating power be turned off. Trigger out is also asserted if a trigger crowbar input signal is asserted.

Trigger circuit 200 includes a PNP bipolar transistor Q1, an NPN bipolar transistor Q2, and a diode D1. Diode D1 is coupled to Vcc (supply voltage), which in the preferred embodiment is 17 volts. Diode D1 has an anode coupled to Vcc to conduct current from Vcc. Trigger circuit 200 includes a resistor 201 coupled in series to a cathode of diode D1 and capacitor 202 coupled between resistor 201 and ground. An emitter of transistor Q1 is coupled to a node N1 between resistor 201 and capacitor 202.

A capacitor 204 couples Vcc to a base of transistor Q1 and a resistor 206 couples node N1 to the base of transistor Q1. A capacitor 208 couples the base of transistor Q1 to ground. A collector of transistor Q1 provides the trigger output signal.

A resistor 210 couples a collector of transistor Q2 to the base of transistor Q1. An emitter of transistor Q2 is coupled to ground and a base of transistor Q2 receives the trigger crowbar input signal. In the preferred embodiment, capacitor 202 is rated at about 10 microfarads and 25 volts, and capacitor 204 and capacitor 208 are 0.01 microfarad capacitors.

In operation, while power is provided to trigger circuit 200, current flows through diode D1 and resistor 201 to charge capacitor 202. Capacitor 204 couples the supply voltage to the base of transistor Q1, making transistor Q1 nonconducting. Assertion of the trigger crowbar input signal turns transistor Q2 on, forcing the voltage potential at the collector of transistor Q2 low. The low potential at the collector of transistor Q2 causes the potential at the base of transistor Q1 to go low, turning it on. Turning transistor Q1 on results in vcc providing current to assert the trigger out signal. The current is supplied from charge stored in capacitor 202, which is more slowly, and at a lower current, charged through D1 and resistor 201.

When power is removed from the system, the supply voltage drops to zero. The supply voltage level is coupled to the base of transistor Q1 by capacitor 204. When the voltage level at the base of transistor Q1 has fallen low enough, transistor Q1 will be turned on. While supply voltage coupled to the emitter of transistor Q1 is no longer available to assert the trigger out signal, capacitor 202 is large enough to store sufficient charge to assert the trigger out signal.

As described above, asserting the trigger out signal to SCR crowbar 130 shown in FIG. 2 removes charge from storage capacitor 120. A combination of the resistance of series resistor 132 and the capacitance of storage capacitor 120 defines the time constant for removing the charge from storage capacitor 120. As the maximum high-voltage capacitance used for storage capacitor 120, in the preferred embodiment, is about 50 microfarads, and the resistance of series resistor 132 is about 1000 ohms, the worst-case time constant for discharge through SCR crowbar 130 is about 50 milliseconds. This also reduces the chances of arc-over through the capacitor selection switch when the capacitor selection switch is changed. Various high-voltage capacitors are selected by a capacitor switch. If the switch were rotated with one capacitor partially charged, arc-over would occur. However, by the time the pulse buttons are reversed and the hand moved to select another capacitor, the SCR crowbar will have dumped the charge.

Figure 5:
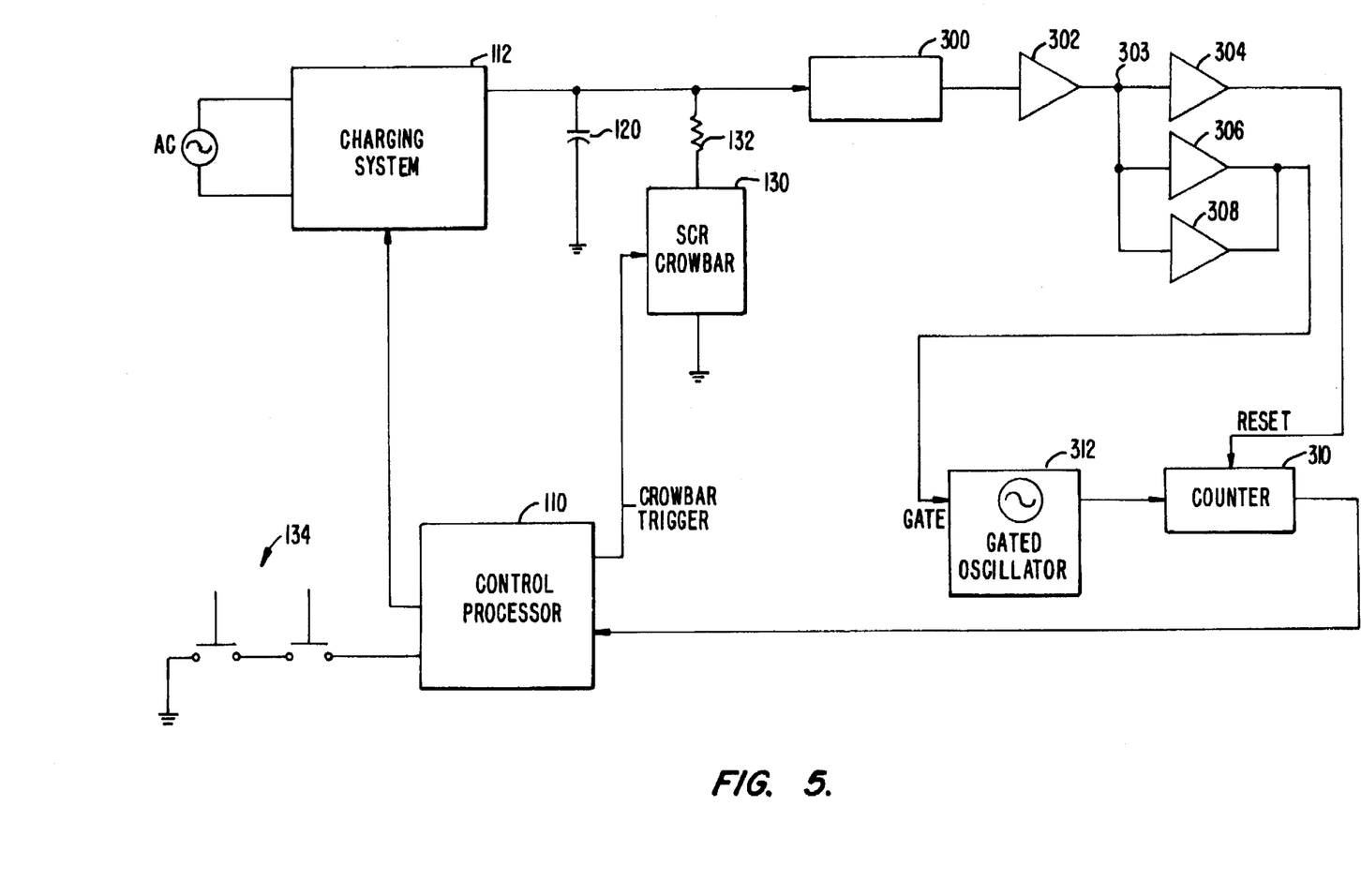
FIG. 5 is a schematic diagram of a preferred embodiment of the present invention including a capacitance measuring apparatus.

FIG. 5 is a schematic diagram of a preferred embodiment of the present invention for transfection system 100 including a capacitance measuring apparatus. As described above, transfection system 100 is a capacitive discharge system that uses large film and electrolytic capacitors to store the necessary charge used in the system. A time constant of the discharge, and the duration of the discharge is determined by the load and the particular capacitor used. An exponential waveform is desirable, as it is gentler on cells than a much-easier-to-generate square wave. Since the time constant depends on capacitance, it is desirable to obtain an actual capacitance value of the storage capacitor, at the time of use. Capacitance values change over time, and capacitance can be a function of impressed voltage and frequency. Therefore, it is desirable to provide a system that not only measures capacitance at the time of use, but also measures capacitance in a procedure that is similar to actual use.

The use of SCR crowbar 130 facilitates measurement of the capacitance of storage capacitor 120 through addition of a voltage divider 300, an amplifier 302, three voltage comparators (comparator 304, comparator 306, and comparator 308), a counter 310 and a gated oscillator 312.

Voltage divider 300 scales the voltage present on storage capacitor 120. The scaled voltage is provided to amplifier 302. Amplifier 302 is a buffer, and drives a node 303 at the scaled voltage level. Each of the voltage comparators, voltage comparator 304, voltage comparator 306 and voltage comparator 308, has an input coupled to node 303. Comparator 304 is set to assert a reset signal to counter 310 when the voltage level at node 303 exceeds a prespecified value. Comparator 306 and comparator 308 together make up a window comparator. Outputs of comparator 306 and comparator 308 are wired-OR to produce an AND function from the comparators and to provide a gate ON signal to gated oscillator 312 when the voltage level is between two prespecified voltage levels. An output of gated oscillator 312 is provided to counter 310.

In operation, voltage divider 300 scales the high voltage stored on storage capacitor 120 to a lower voltage level. It is desirable that, at the lowest output voltage, the peak of the scaled waveform be at least 220 volts. Comparator 304 is set, in well-known fashion, to assert the reset signal when the voltage level at node 303 exceeds 220 volts. The reset signal clears counter 310.

Comparator 306 asserts the gate signal when the voltage level at node 303 falls below 200 volts. Similarly, comparator 308 asserts the gate signal as long as the voltage level at node 303 exceeds (about 73.58) volts. As long as the voltage remains between 200 volts and about 73.58 volts, the gate signal is asserted to gated oscillator 312. The duration of the window represents the time for the voltage at node 303 to drop to the time constant value because the voltage ratios are 1/e. For a waveform $$T = \gamma \text{Ln} \left| \frac{EF - Ei}{EF - Ex} \right|,$$

since EF=Φ, $$T = \gamma \text{Ln} \left| \frac{Ei}{Ex} \right|.$$

If this ratio of $$\frac{Ei}{Ex} = \frac{1}{e},$$

T=γ=time constant. Thus the window pulse-width is exactly equal to the time constant. Counter 310 is driven by oscillator 312, and oscillator 312 only runs during the window. The value of counter 310 is thus proportional to the time constant.

The capacitance measuring system is produced by first charging storage capacitor 120, and thereafter discharging it through a known resistance. If the resistance value is known, as it is when the crowbar is activated, counter 310 produces counts that are proportional to the capacitance of storage capacitor 120, rather than a count that is proportional to a time constant that is, in turn, a product of capacitance and resistance. However, if the crowbar is not triggered, the use of the comparators, gated oscillator and counter measures time constant directly, another parameter provided for readout. By using the shunt circuit that includes series resistor 132 (having a known resistance), the transfection system 100 includes the desired improvement, measuring capacitance directly, measuring time constant and measuring the capacitance under conditions similar to actual use to improve accuracy.

Figure 6:
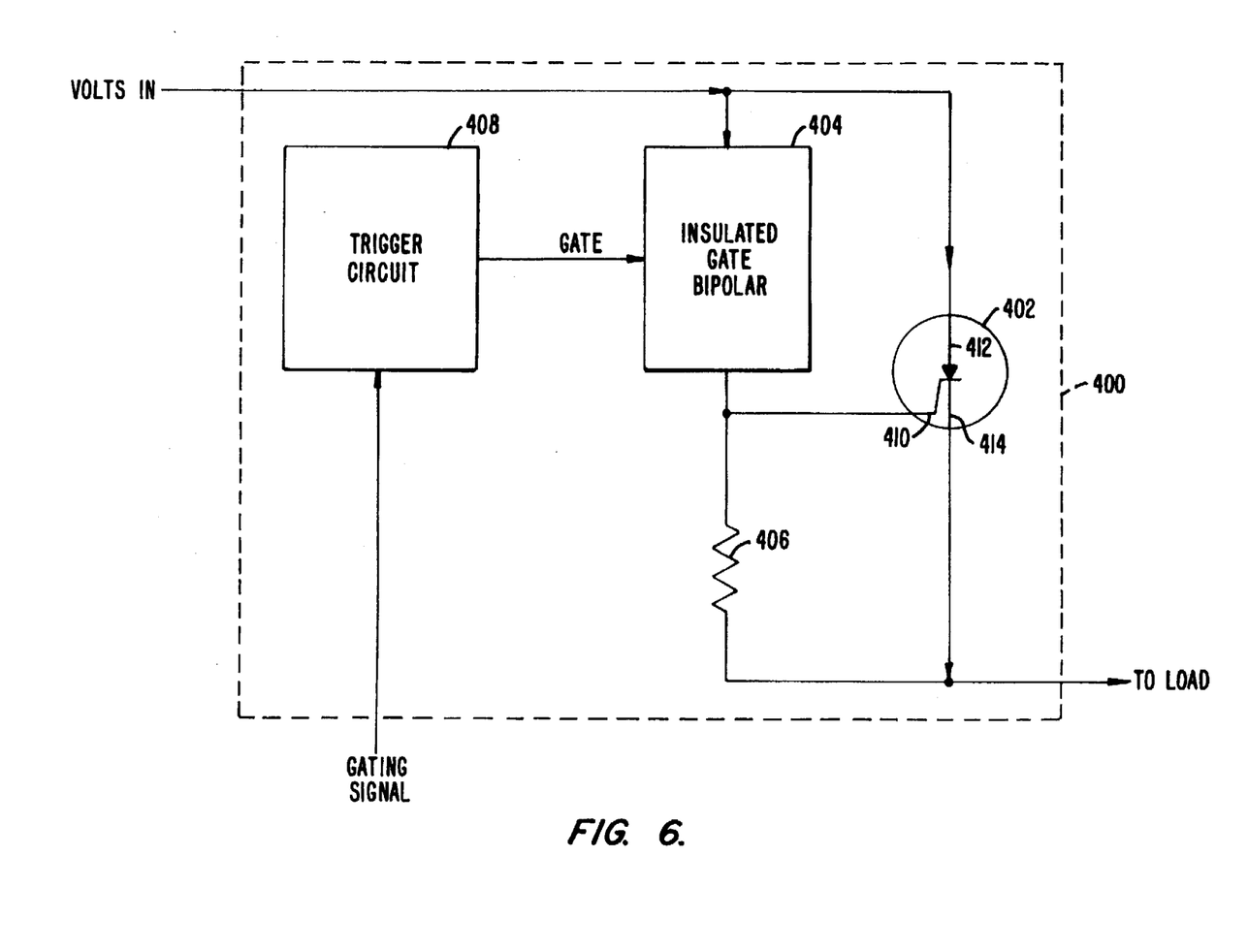
FIG. 6 is a schematic diagram of a preferred embodiment for a low-voltage, high current, low dropout hi-joule switch circuit.

FIG. 6 is a schematic diagram of a preferred embodiment for a low-voltage, high-current, low-dropout hi-joule switch circuit 400. Driver circuit 400 includes an SCR 402. Driver circuit 400 may, therefore, be used in transfection system 100 shown in FIG. 2 as the hi-joule switch 114. Driver circuit 400 includes an insulated gate bipolar transistor 404 in parallel with SCR 402. Transistor 404 does not turn off with holding current. Thus, the parallel combination of SCR 402 and transistor 404 provide advantages of both driver types: SCR 402 provides the clean output waveforms at high voltages and currents, and the bipolar transistor 404 provides the low voltage operation. Driver circuit 400 further includes a current sense resistor 406 and a trigger circuit 408.

SCR 402 includes a gate 410 coupled to an output of transistor 404, an anode 412 coupled to an input of driver circuit 400, and a cathode 414 coupled to an output of driver circuit 400. A collector of transistor 404 is coupled to anode 412, a gate of transistor 404 is coupled to an output of trigger 408, and an emitter of transistor 404 is coupled to gate 410.

Current sense resistor 406 couples gate 410 to cathode 414. Trigger circuit 408 receives a gating signal to activate driver circuit 400.

In operation, transistor 404 is made to stay on until storage capacitor 120 (shown in FIG. 2) is almost fully discharged. Transfection system 100 of FIG. 2 includes a comparator (not shown) that indicates to control processor 110 when the output waveform delivered to load 104 has dropped to less than five volts.

Transistor 404 is only operable when driving output currents up to current levels of about thirty amperes. In the preferred embodiment, current sense resistor 406 is about 0.1 ohm, allowing it to determine when transistor 404 is driving about fifteen amperes to the output. Fifteen amperes through current sense resistor 406 produces a voltage at gate 410 sufficient to trigger SCR 402.

When SCR 402 triggers, it effectively shorts out transistor 404, directing most of the current at the input of driver circuit 400 through itself to the output. When the input voltage decreases below the holding current of SCR 402, transistor 404 automatically resumes operation. Trigger circuit 408 is responsible for providing a sufficient voltage to operate transistor 404 in response to the gating signal. In the preferred embodiment, trigger circuit 408 also isolates the gate voltage from ground.

Depending upon the particular application, if higher voltages are desired than is possible from a single driver circuit 400, two or more driver circuits like driver circuit 400 are added in series to boost output drive capability. In the preferred embodiment, driver circuit 400 incorporates a protection resistor of about 0.5 ohms (not shown) in series with the output to limit maximum current. Driver circuit 400 delivers a maximum output voltage of about 500 volts (though it is operable to about 600 volts), therefore maximum output current will be about 1000 amperes.

Figure 7:
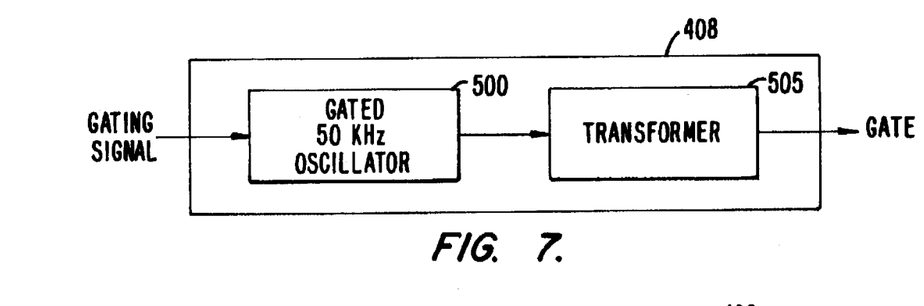
FIG. 7 is a block diagram for a trigger circuit used in the low-voltage driver of FIG. 6.

FIG. 7 is a block diagram for trigger circuit 408 used in driver circuit 400 of FIG. 6. In the preferred embodiment, trigger circuit 408 includes a gated 50 KHz oscillator 500 coupled to a transformer/rectifying circuit 505.

Figure 8:
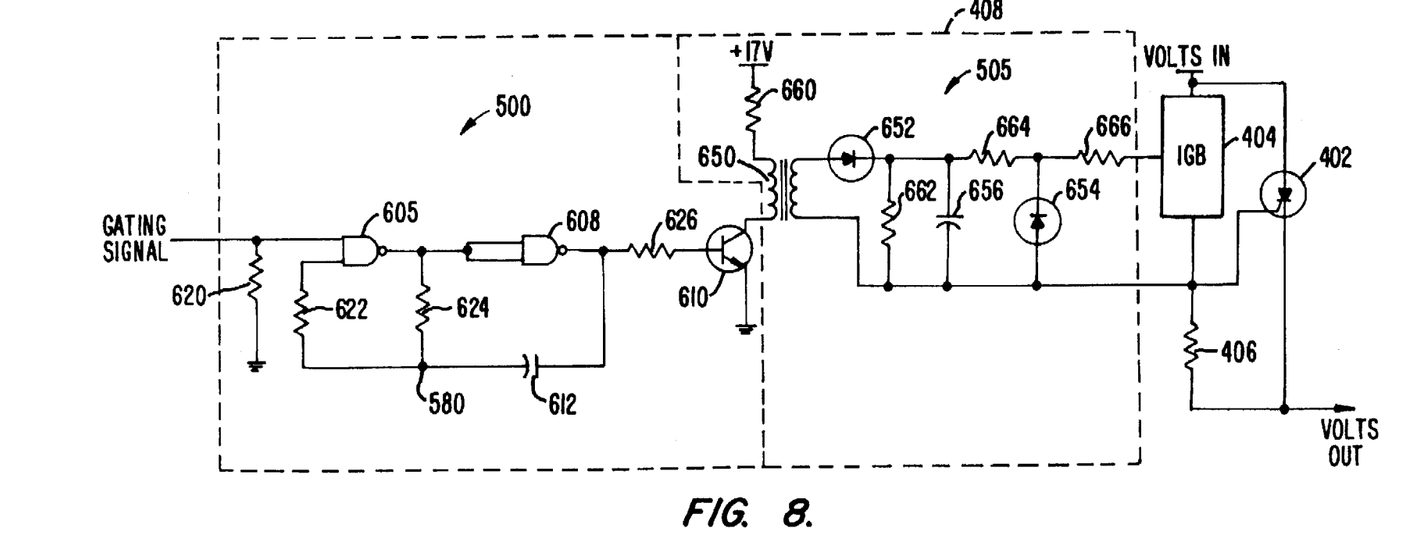
FIG. 8 is a detailed schematic diagram of the low-voltage driver shown in FIG. 6.

FIG. 8 is a detailed schematic diagram of low-voltage driver 400 shown in FIG. 6 illustrating a preferred embodiment of trigger circuit 408. In FIG. 8, oscillator 500 includes two dual-input NAND gates (NAND gate 605 and NAND gate 608), an NPN transistor 610, a capacitor 612, and four resistors (resistor 620, resistor 622, resistor 624 and resistor 626).

Resistor 620 couples the input gating signal to ground. NAND gate 605 has a first input coupled to the ungrounded terminal of resistor 620. One terminal of resistor 622 is coupled between the second input of NAND gate 605 and a node 580. Resistor 624 couples an output of NAND gate 605 to node 580. Both inputs of NAND gate 608 are coupled together and coupled to the output of NAND gate 605. Capacitor 612 couples an output of NAND gate 608 to node 580. Resistor 626 couples the output of NAND gate 608 to a base of transistor 610. An emitter of transistor 610 is coupled to ground. A collector of transistor 610 is coupled to a primary winding terminal of transformer 650 (which is coupled to 17 volts through resistor 660) of transformer/rectifier circuit 505. In response to a gate signal, oscillator 500 operates at about 50 KHz and drives transformer 650.

Transformer/rectifier circuit 505 includes a transformer 650, a diode 652, a zener diode 654, a capacitor 656, and four resistors (resistor 660, resistor 662, resistor 664 and resistor 666). Transformer 650 includes a primary winding and a secondary winding. Resistor 660 couples Vcc to a terminal of the primary winding opposite from transistor 610. Diode 652 and resistor 662 provide a half-wave rectifier, smoothed by capacitor 656. Zener diode 654 regulates the output waveform at the desired voltage to drive insulated gate bipolar transistor 404. In the preferred embodiment, the voltage at the gate of transistor 404 is about 15 volts.

Figure 9:
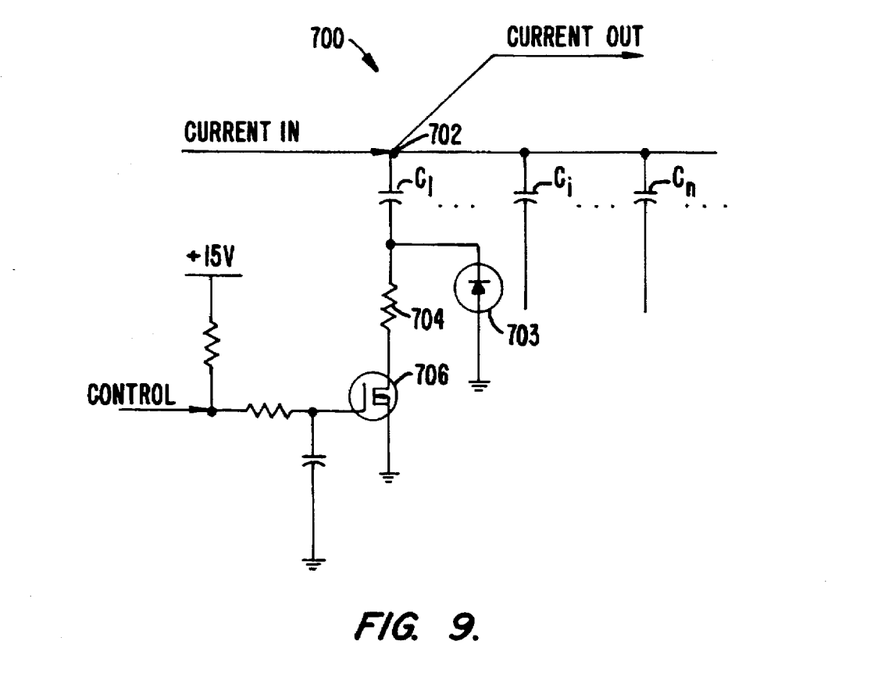
FIG. 9 is a detailed schematic diagram of a preferred embodiment for a capacitor expansion module.

FIG. 9 is a detailed schematic diagram of a preferred embodiment for a capacitor expansion module 700. An expansion module allows low-voltage (500 volt) electrolytic capacitors to be added to the transfection system 100 shown in FIG. 2 in place of storage capacitor 200. The expansion module includes a plurality of capacitors, thus it is desirable to provide for electronic switching to select particular ones of the capacitors of the expansion module. Additionally, since the electrolytic capacitors are rated for a maximum of 500 volts, and the typical maximum load is 20 ohms, the switching control of the expansion module must be able to handle 25 ampere currents. Additionally, the expansion cell desirably permits two or more capacitors to be added in parallel.

Expansion module 700 includes a plurality of electrolytic capacitors, $C_1$ through $C_n$. Each capacitor has a first terminal coupled to a charging node 702. Charging system 112 (shown in FIG. 2) provides charging current to node 702, in the preferred embodiment of about 200 milliamperes, peak (actually a series of 200 milliamperes peak pulses at about 35 KHz and about 33% duty cycle). Coupled to each capacitor is a cell that includes a high-power diode 703, a current limiting resistor 704 and a power FET (or insulated gate bipolar transistor) 706. In a cell, a cathode of diode 703 is coupled to a second terminal of capacitor $C_i$. Diode 703 includes an anode that is grounded. Thus, capacitor $C_i$ can only discharge using diode 703.

Additionally, current limiting resistor 704 has one terminal coupled to the cathode of diode 703 and a second terminal coupled to a source of FET 706. A drain of FET 706 is coupled to ground. A control signal activates or deactivates FET 706, depending upon whether the capacitor $C_i$ in its cell is to be charged.

In operation, a control signal is asserted to each FET 706 in every cell that includes a capacitor $C_i$ to be charged. Charging current at charging node 702 charges only those capacitors in cells having FET 706 activated. Current does not flow through diode 703 during capacitor charging. Current limiting resistor 704 limits maximum current in FET 706. Current in a particular capacitor $C_i$ can exceed the charging current maximum provided from the charging system, such as when a FET 706 is activated when another capacitor $C_i$ in parallel stores a charge.

For discharging the capacitors $C_i$, it does not matter which cells have an activated FET 706, all capacitors are discharged. Capacitors $C_i$ discharge through diode 703 (a high power diode such as MR756) that is capable of handling current surges of over 1000 amperes for short pulses.

Thus, expansion module 700 permits only selected capacitor cells to be activated for charging in parallel, and all charged cells to be discharged, in parallel. The switching is electronically controlled and safe for the switching components. As a result, expansion module 700 uses twelve electrolytic capacitors (a 25 microfarad capacitor, a 50 microfarad capacitor, and ten 100 microfarad capacitors) to produce forty-three different capacitance values with 25 microfarad precision.

An expansion module according to a preferred embodiment (Plus module) includes two 1100 microfarad capacitors to provide a 25–3275 microfarad range (131 values) with 25 microfarad precision. The expansion module also includes a 40 microfarad capacitor (a dither capacitor). A mode controlled by the control processor allows, by utilizing the capacitor measuring function using the SCR crowbar, the microprocessor to measure all of the capacitors. Hence, the microprocessor then has information as to the capacitance value at close to time of use. Hence, when the operator selects a desired capacitor, the microprocessor sorts out the best combination to produce the actual capacitance value desired. This procedure allows ±20% capacitors to be turned into ±10% capacitors. This procedure is an important feature of the preferred embodiment of the transfection system.

In conclusion, the present invention provides a simple, efficient solution to a problem of molecular biology. While the above is a complete description of the preferred embodiments of the invention, various alternatives, modifications, and equivalents may be used. Therefore, the above description should not be taken as limiting the scope of the invention which is defined by the appended claims.

What is claimed is:

1. A capacitor expansion module, comprising:
   a plurality of capacitors, each having a first terminal adapted to be coupled in parallel to a charging node; and a plurality of corresponding electronic control circuits, each one of said plurality of corresponding electronic control circuits coupled to a second terminal of a corresponding one of said plurality of capacitors, each corresponding electronic control circuit comprising:

a power diode having an anode coupled to a reference voltage and a cathode coupled to said second terminal of said corresponding capacitor;

a resistor having a first terminal coupled to said second terminal of said corresponding capacitor; and a power field-effect transistor having a drain coupled to said reference voltage, a source coupled to a second terminal of said resistor and a gate, said power field-effect transistor responsive to a control signal to permit current to flow from said source to said drain;

wherein assertion of said control signal to selected ones of said power field-effect transistors of said plurality of control circuits permits charging of only those ones of said plurality of capacitors that correspond to said selected ones of said power field-effect transistors.

2. A capacitor expansion module, comprising:

a plurality of capacitors, each having a first terminal adapted to be coupled in parallel to a charging node; and means for individually selecting selected ones of said plurality of capacitors;

means, coupled to a second terminal of each of said plurality of capacitors, for charging only said selected ones of said plurality of capacitors while permitting all charged capacitors to be discharged.

3. A method for operating a transfection system adapted to deliver a high-voltage current to a chemical solution from a capacitor expansion module, with the expansion module including a plurality of capacitors coupled in parallel wherein the plurality of capacitors provide a plurality of nominal capacitance values varying from each other by a nominal increment and wherein the capacitance values each have an associated precision tolerance, comprising the steps of:

including a dither capacitor in the expansion module having a nominal capacitance value not equal to an even multiple of the nominal increment and having a tolerance value equal to the associated precision tolerance;

measuring an actual capacitance value of each of the plurality of capacitors of the expansion module after installation in the transfection system;

selecting a desired one of the nominal capacitance values; and choosing a combination of the plurality of capacitors that provide a combination of said actual capacitance values that vary from said desired one capacitance value less than the associated precision tolerance.

* * * * *